United States Patent [19]

Lee

[11] Patent Number: 4,935,530

[45] Date of Patent: Jun. 19, 1990

[54] PROCESS FOR PREPARING 5-SUBSTITUTED-3-FURALDEHYDES

[75] Inventor: Gary C. M. Lee, Laguna Hills, Calif.

[73] Assignee: Allergan, Inc., Irvine, Calif.

[21] Appl. No.: 259,225

[22] Filed: Oct. 18, 1988

[51] Int. Cl.$^5$ .............................. C07D 307/34
[52] U.S. Cl. .................... 549/214; 549/209; 549/318; 549/320; 549/321; 549/322; 549/323; 549/324; 549/473; 549/479; 549/480; 549/484
[58] Field of Search .............. 549/214, 209, 473, 479, 549/480, 484, 318, 320, 321, 322, 323, 324

[56] References Cited

U.S. PATENT DOCUMENTS

| 4,195,026 | 3/1980 | Kraus | 549/214 |
| 4,221,585 | 9/1980 | Levitt | 549/479 |
| 4,500,520 | 2/1985 | Haber | 549/214 |

OTHER PUBLICATIONS

Tetrahedron Letters, vol. 24 (52), pp. 5835–5838, 1983.
Tetrahedron Letters, vol. 26 (47), pp. 5827–5830, 1985.
Tetrahedron Letters, vol. 27 (38), pp. 4533–4536, 1986.

*Primary Examiner*—Glennon H. Hollrah
*Assistant Examiner*—Ba K. Trinh
*Attorney, Agent, or Firm*—Martin A. Voet

[57] ABSTRACT

A process for preparing 5-substituted-3-furaldehydes which comprises reacting 3-furaldehyde with lithium morpholide, followed by sec-butyl lithium, followed by an electrophile.

7 Claims, No Drawings

PROCESS FOR PREPARING 5-SUBSTITUTED-3-FURALDEHYDES

This invention relates to a new process for preparing 5-substituted-3-furaldehydes. These compounds are useful as intermediates for making pharmaceutically active furanones. For example, 5-trialkylsilyl-3-furaldehydes are useful as intermediates for preparing manoalide and manoalide analogs having anti-inflammatory activity.

BACKGROUND OF THE INVENTION

Metallation (lithiation) of 3-furaldehyde is reported by Comins, et al., *J. Org. Chem.*, 52:104–109 (1987) to occur at the 2-position with high regioselectivity.

Goldsmith, et al., *Tetrahedron Letters* 24:5835–5838 (1983) prepared 5-trimethylsilyl-3-hydroxymethylfuran by first blocking the 2-position of 3-hydroxymethylfuran with a phenylmercapto group, then introducing the trimethylsilyl group into the 5-position and removing the phenylmercapto from the 2-position. This multi-step process was used by Katsumura, et al., *Tetrahedron Letters* 26:5827–5830 (1985), in a synthesis of manoalide, to prepare 5-trimethylsilyl-3-hydroxymethylfuran which was then oxidized to give 5-trimethylsilyl-3-furaldehyde.

DESCRIPTION OF THE INVENTION

This invention relates to a new process for preparing 5-substituted-3-furaldehyde compounds. This process can be carried out as a one pot process, that is without isolation of intermediates. It is unexpected, in view of the teaching of the art described hereinabove, that in the process of this invention, metallation occurs at the 5-position of 3-furaldehyde and the 5-substituted-3-furaldehydes are prepared from 3-furaldehyde without first blocking the 2-position.

The process of this invention may be represented as follows:

A process for preparing 5-substituted-3-furaldehydes of the formula:

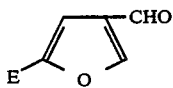

in which E is an electrophilic group, which process comprises reacting 3-furaldehyde with:
(1) lithium morpholide, followed by
(2) secondary-butyl lithium, followed by
(3) an electrophile.

Exemplary of the electrophilic groups (E) in this process are trialkylsilyl; trialkylstannyl; $C_{1-20}$ alkyl; $C_{2-20}$ alkenyl or alkynyl where the double or triple bond is at the $C_2$ or greater carbon; or benzyl optionally substituted on the phenyl ring by halo, lower alkyl or lower alkoxy; N-alkylcarbamoyl, alkylmercapto, phenylmercapto or alkanoyl.

Illustrative of the electrophiles which may be used in the process of this invention are halides, aldehydes, ketones, isocyanates, epoxides, disulfides and esters.

Particular electrophiles which may be used in the process of this invention are:
trimethylsilyl chloride
triethylsilyl chloride
t-butyl dimethylsilyl chloride
tributylstannyl chloride
1-iodooctane
2-undecanone
4-bromobenzaldehyde
1-hexanal The process of this invention may be carried out as follows:

3-Furaldehyde is added to a solution of lithium morpholide prepared by reacting n-butyl lithium (in an inert solvent such as hexane) with morpholine in a suitable solvent such as tetrahydrofuran at reduced temperature under an inert gas such as argon. After about 15–30 minutes, sec-butyl lithium in a solvent such as cyclohexane is added and the reaction mixture is stirred at reduced temperature for about 1–8 hours, then the electrophile is added. Stirring is continued for about 8–40 hours, preferably about 10–20 hours, while allowing the temperature of the reaction mixture to rise to room temperature. The reduced temperature referred to above is about −78° C.

The use of 5-substituted-3-furaldehydes as intermediates is illustrated by Katsumura et al., cited hereinabove, who used 5-trimethylsilyl-3-furaldehyde in the synthesis of manoalide and seco-manoalide. Manoalide analogs having anti-inflammatory activity are also prepared from 5-substituted-3-furaldehydes, for example the reaction of 5-trimethylsilyl-3-furaldehyde with an alkylmagnesium bromide and acetic anhydride gives 2-trimethylsilyl-4-α-acetoxyalkylfuran which is treated with singlet oxygen to give a 4-α-acetoxyalkyl-5-hydroxy-2(5H)-furanone.

The following examples are not limiting but are illustrative of the process of this invention. Temperatures are in degrees Centigrade.

EXAMPLE 1

5-Trimethylsilyl-3-furaldehyde n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated down to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48°–50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

MS exact mass calculated for $C_8H_{12}O_2Si$ (M+) 168.0607, found 168.0588.

EXAMPLE 2

5-Triethylsilyl-3-furaldehyde n-Butyl lithium (a 2.5M solution in hexane; 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 7 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsily-3-furaldehyde as a pale yellow oil, boiling point 85°–90°/0.4 torr.

IR (neat) 1680 cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCl$_3$) 2.9, 7.1, 117.2, 128.8, 155.6, 162.3 and 184.6.

MS m/e exact mass calculated for C$_{11}$H$_{18}$O$_2$Si (M+) 210.1076, found 210.1071.

EXAMPLE 3

5-(tert-Butyldimethylsilyl)-3-furaldehyde n-Butyl lithium (a 2.5M solution in hexane; 8.3 ml, 20.8 mmol) was added to a solution of morpholine (1.81 ml, 20 mmol) in tetrahydrofuran (100 ml) at −78° under argon. After 20 min. 3-furaldehyde (1.8 ml, 20.8 mmol) was added. After another 15 min., sec-butyl lithium (a 1.3M solution in cyclohexane; 16.8 ml, 21.9 mmol) was added dropwise and stirring continued at −78° for 1 hour before a solution of t-butyl dimethylsilyl chloride (9.4 g, 62.4 mmol) in tetrahydrofuran (10 ml) was added. Stirring was continued overnight (16 hours) while the cooling bath was allowed to attain room temperature. The solution was poured into ice cold 10% (v/v) hydrochloric acid (40 ml) and after stirring at 0° for 10 min., the layers were separated. The aqueous phase was extracted with diethyl ether. All the organic phases were combined, dried (magnesium sulfate) and evaporated down to give a brown oil, which was distilled under high vacuum to give the title aldehyde, boiling point 80°–5°/0.5 torr., m.p. 37°–8°.

$^1$H NMR (CDCl$_3$) 0.23 (s, 6H), 0.90 (s, 9H), 6.99 (s, 1H), 8.25 (s, 1H) and 9.94 (s, 1H).

$^{13}$C NMR (CDCl$_3$) 16.6, 26.1, 117.3, 128.8, 155.5, 162.7 and 184.5.

MS exact mass calculated for C$_{11}$H$_{18}$O$_2$Si (M+) 210.1076, found 210.1075.

EXAMPLE 4

5-(n-Tributylstannyl)-3-furaldehyde n-Butyl lithium (a 2.5M solution in hexane; 8.7 ml, 22 mmol) was added to a solution of morpholine (1.9 ml, 22 mmol) in tetrahydrofuran (80 ml) at −78° under argon. After 15 min., 3-furaldehyde (1.8 ml, 21 mmol) was added. After another 20 min., sec-butyl lithium (a 1.3M solution in cyclohexane; 19.2 ml, 25 mmol) was added dropwise and stirring continued at −78° for 4 hours before tributylstannyl chloride (8.5 ml, 31 mmol) was added. Stirring was continued at room temperature for 40 h. The solution was poured into ice cold 10% (v/v) hydrochloric acid (30 ml) and after stirring at 0° for 10 min., the layers were separated. The aqueous phase was extracted with diethyl ether. All the organic phases were combined, dried (magnesium sulfate) and evaporated down to give an oil, which was purified by flash chromatography on silica using 5% ethyl ether/hexane. Fractions with R$_f$ of about 0.27 on evaporation gave the title compound as a very pale yellow oil.

$^1$H NMR (CDCl$_3$) 0.93 (m, 9H), 1.15 (m, 6H), 1.35 (m, 6H), 1.65 (m, 6H), 6.95 (s, 1H), 8.35 (s, 1H) and 9.99 (s, 1H).

$^{13}$C NMR (CDCl$_3$) 10.1, 13.5, 17.5, 26.6, 26.7, 27.0, 27.4, 27.8, 28.6, 28.7, 28.9, 117.8, 128.7, 156.3, 165.2 and 184.4.

IR (neat) 2720–2800, 1675 (s,s) and 1125 (s,s).

MS exact mass calculated for C$_{17}$H$_{30}$SnO$_2$ (M+) 384.1257, found 384.1252.

EXAMPLE 5

5-Octyl-3-furaldehyde n-Butyl lithium (a 2.5M solution in hexane; 4.37 ml, 10.9 mmol) was added to a solution of morpholine (0.91 ml, 10.4 mmol) in tetrahydrofuran (40 ml) at −78° under argon. After 20 min., 3-furaldehyde (0.9 ml, 10.4 mmol) was added. After another 20 min., sec-butyl lithium (a 1.3M solution in cyclohexane; 8.4 ml, 10.9 mmol) was added dropwise and stirring continued at −78° for 4 hours before 1-iodooctane (2.07 ml, 11.4 mmol) was added. Stirring was continued overnight (17 hours) while the cooling bath was allowed to attain room temperature. The solution was poured into ice cold 10% (v/v) hydrochloric acid (15 ml) and after stirring at 0° for 10 min., the layers were separated. The aqueous phase was extracted with diethyl ether. All the organic phases were combined, dried (magnesium sulfate) and evaporated to give an oil, which was purified by flash chromatography on silica using 10% ethyl ether/hexane. Fractions with R$_f$ of about 0.23 on evaporation afforded the title compound as colorless needles, m.p. 25° (hexane).

$^1$H NMR (CDCl$_3$) 0.93 (t, 3H, J=7.2 Hz), 1.32 (br, 10H), 1.67 (t, 2H, J=7.1 Hz), 2.68 (t, 2H, J=7.8 Hz), 6.43 (s, 1H), 7.98 (s, 1H) and 9.92 (s, 1H).

$^{13}$C NMR (CDCl$_3$) 13.6, 22.2, 27.1, 27.3, 28.6, 28.7, 28.8, 31.4, 101.3, 129.2, 149.9, 159.0 and 183.9.

MS exact mass calculated for C$_{13}$H$_{20}$O$_2$ (M+) 208.1463, found 208.1454.

EXAMPLE 6

5-(1-Hydroxy-1-methyldecyl)-3-furaldehyde n-Butyl lithium (a 2.5M solution in hexane; 4.37 ml, 10.9 mmol) was added to a solution of morpholine (0.91 ml, 10.4 mmol) in tetrahydrofuran (40 ml) at −78° under argon. After 20 min., 3-furaldehyde (0.9 ml, 10.4 mmol) was added. After another 20 min., sec-butyl lithium (a 1.3M solution in cyclohexane; 8.4 ml, 10.9 mmol) was added dropwise and stirring continued at −78° for 7 hours before 2-undecanone (2.36 ml, 11.4 mmol) was added. Stirring was continued overnight (17 hours) while the cooling bath was allowed to attain room temperature. The solution was poured into ice cold 10% (v/v) hydrochloric acid (30 ml) and after stirring at 0° for 10 min., the layers were separated. The aqueous phase was extracted with diethyl ether. All the organic phases were combined, dried (magnesium sulfate) and evaporated down to give an oil, which was purified by flash chromatography on silica. Fractions with $R_f$ of about 0.07 on evaporation gave the title compound as a yellow oil.

$^1$H NMR (CDCl$_3$) 0.91 (t, 3H, J=7.0 Hz), 1.28 (brs, 14H), 1.58 (s, 3H), 1.85 (m, 2H), 2.10 (br, 1H), 6.62 (s, 1H), 8.03 (s, 1H) and 9.93 (s, 1H).

$^{13}$C NMR (CDCl$_3$) 13.9, 22.5, 23.9, 26.1, 29.1, 29.3, 29.6, 31.4, 31.7, 41.2, 71.2, 101.4, 128.9, 150.7, 162.8 and 184.7.

MS exact mass calculated for $C_{16}H_{26}O_3$ (M$^+$) 266.1881, found 266.1873.

EXAMPLE 7

5-((4-Bromophenyl)-1-hydroxymethyl)-3-furaldehyde n-Butyl lithium (a 2.5M solution in hexane; 4.37 ml, 10.9 mmol) was added to a solution of morpholine (0.91 ml, 10.4 mmol) in tetrahydrofuran (30 ml) at −78° under argon. After 20 min., 3-furaldehyde (0.91 ml, 10.4 mmol) was added. After another 20 min., sec-butyl lithium (a 1.3M solution in cyclohexane; 8.4 ml, 10.9 mmol) was added dropwise and stirring continued at −78° for 4 hours before a solution of 4-bromobenzaldehyde (2.11 g, 11.4 mmol) in tetrahydrofuran (10 ml) was added. Stirring was continued overnight (17 hours) while the cooling bath was allowed to attain room temperature. The solution was poured into ice cold 10% (v/v) hydrochloric acid (30 ml) and after stirring at 0° for 10 min., the layers were separated. The aqueous phase was extracted with diethyl ether. All the organic phases were combined, dried (magnesium sulfate) and evaporated down to give an oil, which was purified by flash chromatography on silica using 40% ethyl acetate/hexane. Fractions with $R_f$ of about 0.23 on evaporation gave the title compound as a yellow solid, m.p. 83°–4° (recrystallized from chloroform).

$^1$H NMR (CDCl$_3$) 2.85 (br, 1H), 5.83 (s, 1H), 6.56 (s, 1H), 7.34 (d, 2H, J=8.4 Hz), 7.55 (d, 2H, J=8.4 Hz), 8.05 (s, 1H) and 9.89 (s, 1H).

$^{13}$C NMR (CDCl$_3$) 68.6, 103.9, 121.9, 128.0, 128.5, 131.4, 138.8, 151.7, 158.2 and 184.9.

MS exact mass calculated for $C_{12}H_9BrO_3$ (M$^+$) 279.9735, found 279.9741.

EXAMPLE 8

5-(1-Hydroxyhexyl)-3-furaldehyde n-Butyl lithium (a 2.5M solution in hexane; 4.37 ml, 10.9 mmol) was added to a solution of morpholine (0.91 ml, 10.9 mmol) in tetrahydrofuran (30 ml) at −78° under argon. After 20 min., 3-furaldehyde (0.9 ml, 10.4 mmol) was added. After another 20 min., sec-butyl lithium (a 1.3M solution in cyclohexane; 8.4 ml, 10.9 mmol) was added dropwise and stirring continued at −78° for 7 hours before 1-hexanal (1.31 ml, 10.9 mmol) was added. Stirring was continued overnight (16 hours) while the cooling bath was allowed to attain room temperature. The solution was poured into ice cold 10% (v/v) hydrochloric acid (30 ml) and after stirring at 0° for 10 min., the layers were separated. The aqueous phase was extracted with diethyl ether. All the organic phases were combined, dried (magnesium sulfate) and evaporated down to give a brown oil, which was purified by flash chromatography on silica using 40% ethyl ether/hexane. Fractions with $R_f$ of about 0.08 on evaporation gave the title compound as a yellow oil.

$^1$H NMR (CDCl$_3$) 0.91 (br, 3H), 1.35 (brm, 6H), 1.86 (m, 2H), 2.25 (br, 1H), 4.72 (t, 1H), 6.74 (s, 1H), 8.05 (s, 1H) and 9.92 (s, 1H).

$^{13}$C NMR (CDCl$_3$) 13.8, 22.4, 24.9, 31.4, 35.2, 67.2, 102.5, 128.9, 151.1, 160.0 and 184.8.

MS exact mass calculated for $C_{11}H_{16}O_3$ (M$^+$) 196.1099, found 196.1099.

EXAMPLE 9

Using methyl isocyanate in place of 1-hexanal in the process of Example 8, 5-N-methylcarbamoyl-3-furaldehyde is prepared.

EXAMPLE 10

By the procedure of Example 8, using diphenyldisulfide in place of 1-hexanal, 5-phenylmercapto-3-furaldehyde is prepared.

EXAMPLE 11

In the procedure of Example 8, using methyl acetate in place of 1-hexanal, 5-acetyl-3-furaldehyde is prepared.

Similarly, using 2,2-dimethyl ethylene oxide in place of 1-hexanal, 5-(2-hydroxy-2-methyl)propyl-3-furaldehyde is prepared.

What is claimed is:

1. A process for preparing compounds of the formula:

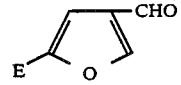

in which E is selected from the group consisting of trialkylsilyl; trialkylstannyl; $C_{1-20}$ alkyl; $C_{2-20}$ alkenyl or alkynyl where the double or triple bond is at the $C_2$ or greater carbon; benzyl optionally substituted on the phenyl ring by halo, lower alkyl or lower alkoxy, N-alkylcarbamoyl, alkylmercapto, phenylmercapto or alkanoyl, which process comprises reacting 3-furaldehyde with:

(1) lithium morpholide, followed by
(2) secondary-butyl lithium, followed by
(3) an E compound.

2. A process for preparing compounds of the formula:

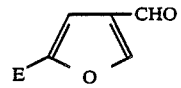

in which E is selected from the group consisting of a halide, aldehyde, ketone, isocyanate, epoxide, disulfide and an ester, which process comprises reacting 3-furaldehyde with:

(1) lithium morpholide, followed by
(2) secondary-butyl lithium, followed by
(3) an E compound.

3. The process of claim 1 in which E is trimethylsilyl, triethylsilyl, or t-butyl dimethylsilyl.

4. The process of claim 3 in which E is trimethylsilyl and the electrophile is trimethylsilyl chloride.

5. The process of claim 1 in which E is tributylstannyl.

6. The process of claim 1 in which E is octyl, 1-hydroxy-1-methyldecyl or 1-hydroxyhexyl.

7. The process of claim 1 in which E is (4-bromophenyl)-1-hydroxymethyl.

* * * * *